United States Patent [19]

Pittala

[11] 4,209,939

[45] Jul. 1, 1980

[54] DOLL USING CIRCULATING FLUID TO SIMULATE BODY TEMPERATURE

[76] Inventor: John Pittala, 214 Asharoken Ave., Northport, N.Y. 11768

[21] Appl. No.: 922,631

[22] Filed: Jul. 7, 1978

Related U.S. Application Data

[63] Continuation-in-part of Ser. No. 725,831, Sep. 23, 1976, abandoned.

[51] Int. Cl.² ............................................. A63H 3/36
[52] U.S. Cl. ......................................... 46/116; 46/162; 128/1 A
[58] Field of Search ................ 46/45, 116, 117, 151, 46/162; 35/17; 128/1 C, 1 R, 1 A

[56] References Cited

U.S. PATENT DOCUMENTS

| 1,536,125 | 5/1925 | Moorman | 35/17 |
| 1,558,278 | 10/1925 | Phillips | 46/116 |
| 2,752,697 | 7/1956 | Lawall | 35/17 |
| 2,774,184 | 12/1956 | Hefferan et al. | 35/17 X |
| 2,859,731 | 11/1958 | Sutton | 128/1 C |
| 3,461,855 | 8/1969 | Brown et al. | 128/1 A |
| 3,562,925 | 2/1971 | Baermann et al. | 35/17 |

Primary Examiner—F. Barry Shay
Attorney, Agent, or Firm—Abraham Saffitz

[57] ABSTRACT

A skin structure in a doll providing simulated body temperature by fluid circulation comprised of two layers separated by studs forming passageways between said layers for the circulation of fluid of the desired temperature to impart on the surface of the doll a temperature approximating body temperature. The controlled temperature fluid may be provided in a reservoir so that the fluid can be circulated to and from the skin structure. The outer skin layer is preferably resilient. The studs are appropriately spaced between the layers and separate said layers. Other creature representations may incorporate the novel spaced layer and stud passageway construction of the invention.

8 Claims, 6 Drawing Figures

U.S. Patent  Jul. 1, 1980  4,209,939
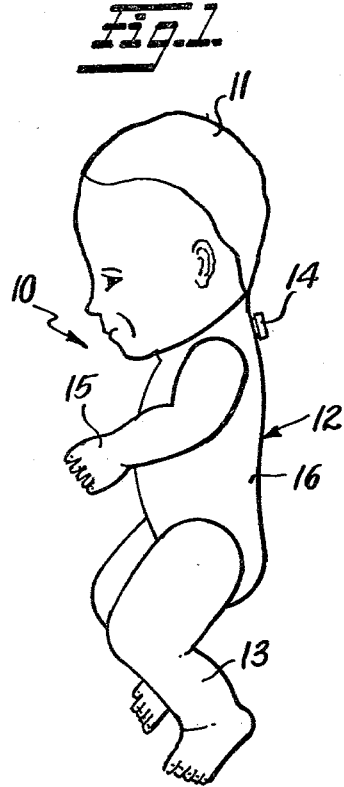
*fig.1.*
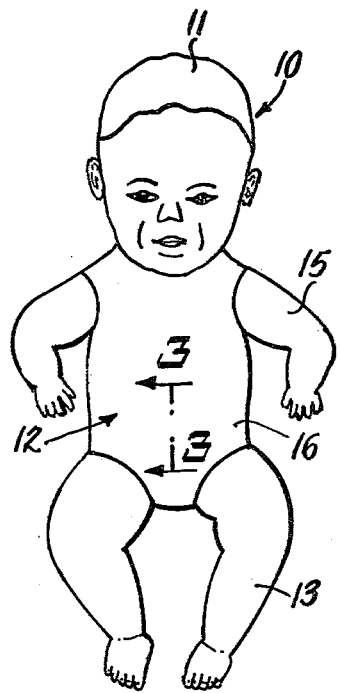
*fig.2.*
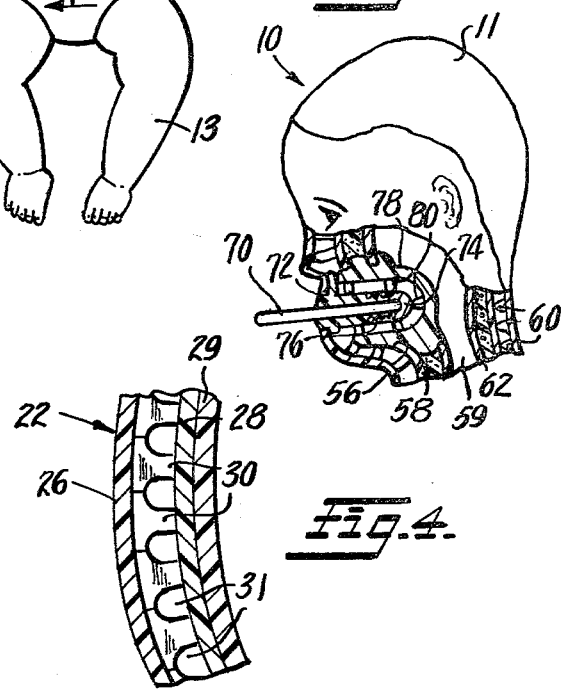
*fig.7.*
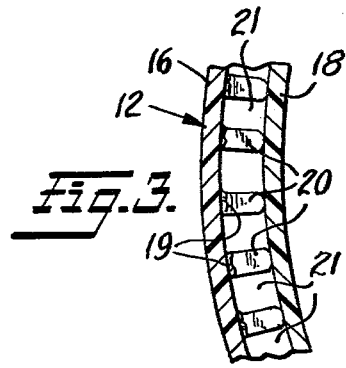
*fig.3.*
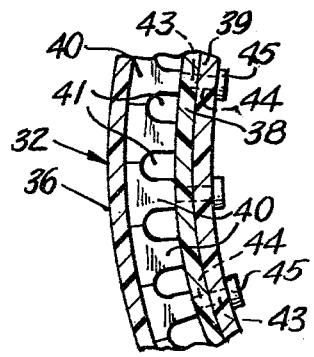
*fig.5.*
*fig.4.*
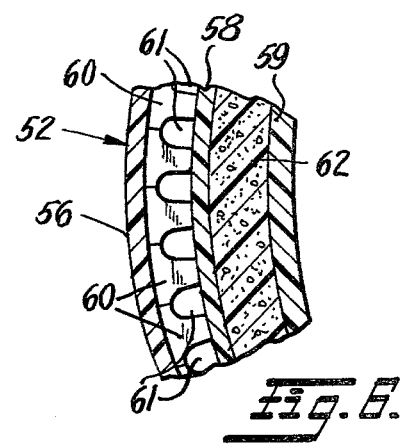
*fig.6.*

DOLL USING CIRCULATING FLUID TO SIMULATE BODY TEMPERATURE

CROSS REFERENCE TO RELATED APPLICATION

This is a continuation-in-part application of my prior application, Ser. No. 725,831, filed Sept. 23, 1976 and entitled *Creature Representation or Doll Having Fluid Circulating System to Simulate Body Temperature*, now abandoned.

BACKGROUND OF THE INVENTION

1. Field of the Invention

The invention relates to creature representations such as flexible figure toys, robots, models, and dolls of the type having heating means and being made of special materials in which a warming fluid is circulated within and near the skin of the doll to thereby serve educational and amusement purposes.

2. Description of the Prior Art

U.S. Pat. No. 3,154,881 discloses a doll incorporating a resistance wire heater 176 as shown in FIG. 10 provided in the throat so that, when a thermometer is inserted in the mouth, the simulated body temperature may be determined.

U.S. Pat. No. 2,752,697 discloses a doll used for instructional purposes having tubes representing arteries and veins extending therethrough through which a liquid representing blood may be circulated. Artificial wounds are provided in the body and the student is taught to locate pressure points to stop the flow of blood through a wound or laceration.

U.S. Pat. No. 3,704,528 shows a display and instructional device in the form of a flat chart with a representation of the human body having transparent tubes representing veins and arteries through which simulated blood is circulated.

DISTINCTION OVER THE PRIOR ART CITED BY THE APPLICANT

None of the above patents disclose the specific circulating tubes wherein the fluid circulates within the supporting structure of a special studded construction comprising two skin layers separated by studs forming passageways between the layers for the circulation of a fluid of a desired temperature.

OBJECTS OF THE INVENTION

An object of the invention is to provide a warm life-like creature representation such as a doll, robot and/or model possessing one of the essential characteristics of living beings, e.g., body warmth, which is safe to use.

A further object of the invention is to provide in a warm life-like creature such as a doll an outer skin structure comprising two skin layers separated by studs optionally forming part of or fastened to a supporting shell which surrounds the warming fluid circulating system and electrically heated reservoir within the body of the representation. The invention contemplates the use of elastic layers such as foam rubber or synthetic elastomers on either or both of the outer surfaces of the skin layers to simulate human skin in appearance and to the touch.

Other and further objects of the invention will become apparent from the following summary of the invention, the drawings and the detailed description of the preferred embodiment.

SUMMARY OF THE INVENTION

A heated creature representation such as a doll having a unique two layer skin structure separated by studs through which controlled temperature fluid is circulated to impart on the surface of the doll a simulated body temperature. The interior of the doll may be provided with a heated reservoir, known to the art, containing a controlled temperature fluid and circulating tube means through which the fluid can flow, the design and fabrication of none of these components being part of this disclosure. The like-like appearance and feel of the doll is provided by the novel skin structure surrounding the fluid circulating through parts of the doll, this structure comprised of two layers separated by studs with optional additional material layers, such as foam rubber, synthetic plastic, natural rubber or synthetic elastomer, on either or both of the outer sides of this structure to provide color, texture, resiliency and realistic appearance, as desired. A well means is provided for insertion of a thermometer to detect a range of simulated temperatures perceived through touch of the skin of the doll. This well means for the thermometer or temperature detecting device may be in an oral location or in a rectal location.

BRIEF DESCRIPTION OF THE DRAWINGS

FIG. 1 is a side elevational view of the doll of the present invention;

FIG. 2 is a front view of the doll of FIG. 1;

FIG. 3 is an enlarged, fragmentary, vertical, sectional view of the inner and outer skin layers taken along the section line 3—3 of FIG. 2;

FIGS. 4, 5 and 6 are modifications of the inner and outer skin layers of the doll in the section line relationship of FIG. 3 to thereby illustrate alternate embodiments of the invention.

DESCRIPTION OF THE PREFERRED EMBODIMENTS

As shown in the drawings in FIGS. 1 and 2, the creature representation takes the form of a doll 10 comprising a head 11, a trunk 12, legs 13 and arms 15. The trunk 12 is provided with a removable plug 14 for filling the novel surface structure of the invention. Trunk 12, FIG. 3, shows this structure.

The various embodiments of body surface structure are also represented in a sectional view in FIGS. 3, 4, 5 and 6, a simple embodiment of body surface structure 22 being illustrated in FIG. 4, a variation of this body surface structure being identified by reference numeral 32 in FIG. 5, and still a different variation of this body surface structure being identified in FIG. 6 by reference numeral 12.

The particular portion of the trunk which is selected for the embodiments of surface structure in FIGS. 3, 4, 5 and 6 could also have been taken in an arm or leg section of arm 15 or leg 13 but for purposes of simplicity, the arm and leg portions have not been modified. Obviously it is within the spirit of the invention to do so.

As is apparent in FIGS. 1 and 2 of the drawings, head 11, arms 15, legs 13 and truck 12 are arranged in conventional fashion. Liquid, such as water, may be poured into the opening which is plugged by filler plug 14 and circulated within the passageways of the separate embodiments of the surface structure represented in FIGS. 3, 4, 5 and 6.

The surface structure in each of these embodiments of the body portion of trunk 12 have in common an outer skin layer, an inner skin layer, and a plurality of substantially equally longitudinally separated studs between the outer and inner skin layers. The simplest form of the basic body surface structure is best shown in FIG. 3, the outer skin layer being identified by reference numeral 16, the inner skin layer being identified by reference numeral 18, the intermediate studs being identified by reference numeral 20 and the longitudinal separation of the studs defining passageways being identified by reference numeral 21. It is in these passageways 21 that a heated fluid may be circulated to impart a feeling of warmth to the outer skin layer 16.

Obviously, there are many different ways of providing a simple, spaced apart body surface structure of inner and outer skin layers in order to achieve the desired construction of passageways in the intermediate layer between the studs for circulating a heated fluid to impart warmth to the outer skin layer. First, the connection between the studs 20 and the two skin layers 16 and 18 respectively may be in any suitable form to achieve a tight connection at the ends of each stud. A simple connection is accomplished with an adhesive as shown in FIG. 3 but the connection may also be by means of a fastener head 43 which projects from the apertures 44 for mechanical connection in the body surface structure 32 of FIG. 5.

The adhesive connection in FIG. 3 at the junction of adhesive 19 illustrates the body surface structure in which the outer skin layer 16 is in the form of a flat sheet with a plurality of studs 20 attached thereto. The inner skin layer 18 is molded with the projecting studs integrally connected thereto. If repair is required, a replacement stud can be inserted by merely applying adhesive to each end thereof and positioning said replacement stud in the necessary location between the two skin layers.

Obviously, the premolded stud layer can be reversed, e.g., instead of having the inner skin layer 18 premolded with stud elements 20 for engagement by means of adhesive 19, the outer skin layer 16 can become the premolded surface structure. In this reversed case, the studs are attached to the outer skin layer and the inner skin layer is a flat sheet. The adhesive 19 affixes the free ends of studs 20 to the flat inner skin layer 18.

Still another possibility exists of having both the inner and outer skin layers premolded with projecting studs, each of which are identical, and each of which are joined at their flat free ends by adhesive 19.

It is an advantage of the invention that the outer skin layer 16 and the inner skin layer 18 may be provided in a wide selection of materials such as natural resin (cellulose acetate), synthetic resin (vinyl chloride resin), synthetic rubber (butadiene rubber), natural vulcanized rubber in sheet form, foamed natural or synthetic rubber having a smooth skin surface, including urethane rubber, and a wide variety of soft or semi-rigid plastic materials. The material which is selected for these skin layers is limited only in that it must provide a realistic texture through which a feeling of warmth may be discerned when a heated fluid is circulated therethrough.

In FIG. 4 there is illustrated an embodiment of body surface structure 22 wherein the studs 30 are a separate molded structure having a widened base portion adjacent the outer skin layer 26, which is of uniform thickness. The inner skin layer 28 is also of uniform thickness. The widened base portion of the studs 30 and the split separation at the base of the semicircular passageway 31 facilitates the bonding of the outer skin layer 26 to the studs 30 and also facilitates adhesive bonding to the inner skin layer 28. Since the FIG. 4 assembly is shown prior to application of the adhesive, the adhesive layer is not shown. The use of a shell 29 is illustrated in reinforcing relationship to the inner skin layer and on the underside thereof. Thus the FIG. 4 structure is reinforced in a particularly desirable embodiment for a creature representation such as a doll, figure toy, robot or the like which will receive severe wear. The reinforcing shell layer 29 may be made of plastic impregnated woven fiber glass, canvas or solid plastic of rigid construction.

In FIG. 4 the selection of a very soft, thin, supple and resilient sheet material for both skin layers, combined with a rigid shell, permits a unique combination of an array of passageways for warm fluid in a relatively narrow, confined space.

In contrast, the addition of a resilient sponge rubber or foam plastic layer 62, as shown in FIG. 6 between the reinforcing shell 59 and the inner skin 58, serves to modify the texture of the trunk portion and permits one to "poke" into the trunk with the fingers, giving much the same feeling as is experienced with tactile probing of the abdomen of a living creature. This relationship of the supporting shell 59 to the inner skin layer 58 is altered, as compared to FIG. 4, in that the intermediate soft layer 62 serves to provide a resiliency to the end structure while the studs 60 are similar to those in FIG. 4 and provide the passageways 61 for the warm fluid to be circulated between the outer skin layer 56 and the inner skin layer 58.

In FIG. 5 there is illustrated a mechanical connection which is provided for the studs 40 due to the projecting ends 43 which pierce the apertures 44 of the inner skin layer 38, these projections 43 terminating in flat heads 45 which perform the same function as rivets for an aircraft skin. The mechanical connection is accomplished at the lower surface of the inner skin layer 39 and serves a dual purpose, first to anchor each of the studs by piercing the inner skin layer 38 and second to assure the location of the passageways 41 for circulation of heated fluid.

The similarity between the base portion of the plurality of studs is apparent by simple inspection of FIGS. 4, 5 and 6. Contrast this similarity with the difference in the stud construction of FIG. 3.

Briefly summarizing, FIGS. 3, 4 and 6 illustrate adhesive bonding and FIG. 5 illustrates mechanical bonding of the intermediate stud layer to the inner and outer skin layers.

Although the term "shell" has been used to describe the reinforcing structure, it is obvious that the form of a shell is a "sheet" and the terms are interchangeable. When a curved structure is encountered the shell shape is more accurate while a flat expanse might be better described as a sheet.

It is within the scope of the invention to add openings communicating with the intermediate layer so that the temperature of the warm fluid can be measured with a thermometer. Thus, an opening is contemplated, preferably a well, at the mouth or rectal area, or both, of the creature representation.

The creature representation may be hollow or stuffed and could also have interior articulated elements for movement of the extremities.

Having thus disclosed, the invention which I claim is:

1. A creature representation such as a doll, flexible figure toy, robot or the like comprising:
   a body having a trunk, head and limbs simulating an animate creature;
   said trunk having a surface structure comprising an outer skin, an inner supporting sheet structure spaced from said outer skin, and a plurality of studs serving as an intermediate layer between said outer skin and said inner sheet structure and bonded thereto; and
   said studs in said intermediate layer being constructed to form passageways in said intermediate layer between the studs, said trunk having an external, closable filler opening communicating with said passageways for admitting to said trunk surface structure for circulation in said passageways a heated fluid to impart warmth to the outer skin.

2. A creature representation such as a doll, flexible figure toy, robot or the like comprising:
   a body having a trunk, head and limbs simulating an animate creature;
   said trunk having a surface structure comprising a foam underlayer, an inner supporting sheet structure secured to said underlayer, a studded intermediate layer secured to said inner sheet structure and an outer skin fastened to the studs of said intermediate layer; and
   said studs in said intermediate layer being constructed to form passageways in said intermediate layer between the studs, said trunk having an external, closable filler opening communicating with said passageways for admitting to said trunk surface structure for circulation in said passageways a heated fluid to impart warmth to the outer skin.

3. A creature representation as claimed in claim 1 wherein said inner sheet structure is provided with a reinforcing sheet thereunder which is bonded thereto.

4. A creature representation as claimed in claim 2 wherein said foam underlayer is provided with a reinforcing sheet thereunder which is bonded thereto.

5. A creature representation as claimed in claim 3 wherein said studs of said intermediate layer are extended through said reinforcing sheet and fastened thereto by bonding.

6. A creature representation as claimed in claim 4 wherein said studs of said intermediate layer are extended through and secured to said reinforcing sheet by means of bonding.

7. A creature representation as claimed in claim 5 wherein said studs of said intermediate layer are secured to said reinforcing sheet by means of a fastening portion extending from said stud through said reinforcing sheet and having a flat head secured thereto to prevent inadvertent release.

8. A creature representation as claimed in claim 6 wherein said studs of said intermediate layer are secured to said reinforcing sheet by means of a fastening portion extending from said stud through said reinforcing sheet and having a flat head bonded thereto to prevent inadvertent release, said flat head being adjacent on the inside of said reinforcing sheet to thereby pin said foam layer to the assembly.

* * * * *